United States Patent
Pepels et al.

(10) Patent No.: US 7,309,796 B2
(45) Date of Patent: Dec. 18, 2007

(54) PROCESS FOR THE PREPARATION OF 1,2-DIAMINOCYCLOHEXANE-PLATINUM(II) COMPLEXES

(75) Inventors: Andreas Pepels, Hanau (DE); Holger Rauter, Flieden (DE); Ralf-Dieter Schnebeck, Diez (DE); Friedrich Wissmann, Alzenau (DE)

(73) Assignee: W.C. Heraeus GmbH, Hanau (DE)

( * ) Notice: Subject to any disclaimer, the term of this patent is extended or adjusted under 35 U.S.C. 154(b) by 246 days.

(21) Appl. No.: 11/050,382

(22) Filed: Feb. 3, 2005

(65) Prior Publication Data

US 2005/0197389 A1  Sep. 8, 2005

(30) Foreign Application Priority Data

Feb. 5, 2004  (DE)  .................. 10 2004 005 906

(51) Int. Cl.
*C07F 15/00* (2006.01)
*A61K 31/28* (2006.01)

(52) U.S. Cl. ........................ 556/137; 514/492

(58) Field of Classification Search ............... 556/137; 514/492
See application file for complete search history.

(56) References Cited

U.S. PATENT DOCUMENTS

| | | | |
|---|---|---|---|
| 4,169,846 A | 10/1979 | Inagaki et al. | |
| 4,206,208 A | 6/1980 | Gale et al. | |
| 4,452,812 A | 6/1984 | Macquet et al. | |
| 5,008,419 A * | 4/1991 | Yokoi et al. ................. | 556/137 |
| 5,338,874 A | 8/1994 | Nakanishi et al. | |
| 5,420,319 A | 5/1995 | Okamoto et al. | |
| 2006/0041012 A1* | 2/2006 | Menez et al. ................ | 514/492 |

FOREIGN PATENT DOCUMENTS

| | | |
|---|---|---|
| EP | 0 185 225 A | 6/1986 |
| EP | 0 617 043 A1 | 9/1994 |
| JP | 53-031648 | 3/1978 |
| JP | 54-046752 | 4/1979 |
| JP | 61-171496 | 8/1986 |
| JP | 05-194332 | 8/1993 |
| WO | WO 03/004505 A1 | 1/2003 |

OTHER PUBLICATIONS

The European Search Report.
German Search Report dated Feb. 20, 2004.

* cited by examiner

*Primary Examiner*—Porfirio Nazario-Gonzalez
(74) *Attorney, Agent, or Firm*—Norris, McLaughlin & Marcus, PA

(57) ABSTRACT

A process for the preparation of diaminocyclohexane-platinum(II)-dicarboxylates has the following steps:

B Conversion of $K_2PtX_2$ with 1,2-diaminocyclohexane (DACH) to (2):

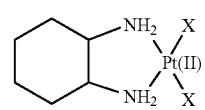

(2)

C Conversion of (2) with too little quantity of silver salt $Ag_nA$ to (3):

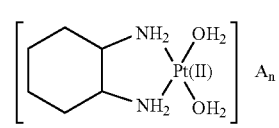

(3)

and removal of the resulting AgX precipitate.

D Conversion of (3) with a dicarboxylate to (1):

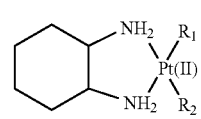

(1)

F Isolation of the product (1),
wherein $R_1$ and $R_2$ together form a dicarboxylato group, X stands for Cl or I, A for a 1-2-valent anion of a mineral acid, and n stands for 1 or 2.

11 Claims, No Drawings

PROCESS FOR THE PREPARATION OF 1,2-DIAMINOCYCLOHEXANE-PLATINUM(II) COMPLEXES

The invention concerns a process for the preparation of 1,2-diaminocyclohexane-platinum(II) complexes, particularly diaminocyclohexane-platinum(II)-dicarboxylate complexes, such as oxaliplatinum.

Cis platinum(II) complexes with 1,2-diaminocyclohexane ligands are used, for instance, as active ingredients for the production of antitumoractive preparations (B. Lippert, ed. Cisplatin, Wiley VCH 1999).

Examples of platinum complexes with antitumor activity are compounds of the formulas (1), (2), (3):

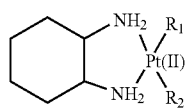
(1)

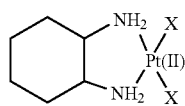
(2)

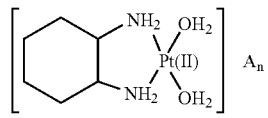
(3)

wherein $R_1$ and $R_2$ together form a dicarboxylato group, X stands for Cl or I, A stands for a univalent or bivalent anion, and n stands for 1 or 2.

The present description of the process for the preparation of cis-platinum compounds refers preferentially to oxaliplatinum [$R_1$ and $R_2$ form together a moiety of the formula (4)]

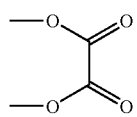
(4)

The task is to prepare diaminocyclohexane-platinum(II)-dicarboxylate complexes of a quality that meets one or more of the following requirements:

1. high purity, particularly lower Ag content;
2. meets or exceeds requirements of the EP (European Pharmacopoeia, 4$^{th}$ edition, 2002, supplement 4.4);
3. no recrystallization is necessary for the purification of the end product;
4. can be obtained in high yield;
5. particular suitability of the active ingredient for parenteral applications.

The task is solved by a process for the preparation of diaminocyclohexane-platinum(II) dicarboxylates with the following steps:

B Conversion of $K_2PtX_2$ with 1,2-diaminocyclohexane (DACH) to (2):

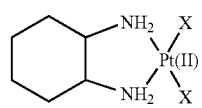
(2)

C Conversion of (2) with a silver salt $Ag_nA$ to (3):

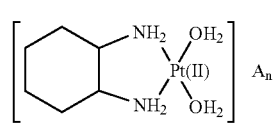
(3)

and removal of the resulting AgX precipitate.

D Conversion of (3) with a dicarboxylate to (1):

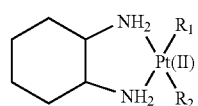
(1)

wherein R1, R2=dicarboxylato;

F Isolation of the product from D; and also if necessary

G Washing of the obtained product with water and methanol (or another low boiling solvent that is pharmacologically acceptable), whereby in step C silver salt are used. Thus during the synthesis, the compound according to formula (2) is converted with less than a stoichiometric amount, i.e. less than 2 mole equivalents of silver salt, in order to ensure a lower silver content in the product.

The optical and isomeric purity of the product of the process depends first on the quality of the chiral ligands 1,2-diaminocyclohexane. It is preferable to use 1,2-diaminocyclohexane of high optical and isomeric purity. Usually products of the required purity are available commercially. If not, commonly used purification processes are available, such as cocrystallization and distillation.

A: $K_2PtCl_4 + 4KI \rightarrow K_2PtI_4 + 4KCl$

During the synthesis it is convenient to start from $K_2PtCl_4$ (optional step A). It is, of course, also possible to start directly from $K_2PtI_4$ (starting from step B). Furthermore, it is also possible to directly convert $K_2PtCl_4$ with DACH. However due to the low solubility of the Ag precipitate, the iodide enhances the prospects for the purity of the end product.

The following characteristics of the procedure have proved to be advantageous. They can be used individually or in combination with each other in the procedure in accordance with the present invention:

C The reaction mixture from the silver reaction is cooled before the filtration to less than 10 degrees C. Thus the precipitate is removed as thoroughly as possible and the product contains little silver.

D The dicarboxylate and/or oxalate is used in the form of its ammonium salt—either as free compound or prepared in situ from dicarbon acid and/or oxalic acid and ammonia.

E Before step F a single or a more beneficial a twofold treatment with activated carbon is carried out conveniently. This leads to a very low content of contaminants particularly with the intermediate product 1,2-diaminocyclohexane-diiodo-platinum(II). After the analysis the end product usually contains less than 0.02% 1,2-diaminocyclohexane-diiodo-platinum.

A-F For all reaction steps purified endotoxin-free water with a limited bacteria content ("purified water" in accordance with EP 4 and/or USP 27) is used. The highly purified water in accordance with EP 4 (European Pharmacopoeia, 4$^{th}$ edition, 2002) is particularly suitable.

F Before the crystallization of the product the solution is filtered via a sterile filter. Thus the resulting product is very well-suited for the preparation of infusion solutions.

G After the last washing process with water, the platinum compound is washed additionally with methanol (or with another low boiling solvent that is pharmacologically acceptable). This leads to very short drying time and less water content (and a small content of aqua species, compound (3)) in the product.

If several or all process steps are combined, the compound produced in accordance with this procedure does not have to be purified by recrystallization in order to meet the specifications required by the European Pharmacopoeia (4$^{th}$ edition).

The compound prepared in accordance with the present invention has no melting point in the range of 198 to 292 degrees C. (as stated in U.S. Pat. No. 5,338,874) also no melting point in the range of 198.3 to 199.7 degrees C. (according to U.S. Pat. No. 5,420,319) and instead shows a decomposition range from 272 to 303 degrees C. more specifically a decomposition range of 286 to 299 degrees C. Yet the crystal structure of the derived platinum compound is identical to the published structure (Lit. Ref.: Bruck, M. A.; et al., Inorg. Chim. Acta, 92 (1984)).

The present invention particularly describes a procedure for the preparation of oxaliplatinum [oxalato-(trans-1-1,2-cyclohexandiamine)platinum(II); CA Reg. No. 61825-94-3] in accordance with formula (1) with the following reaction steps (diagram 1 and diagram 2):

Preliminary Product: Isomer/enantiomer-pure diaminocyclohexane, purified by crystallization with suitable tartrate salts and/or distillation.

First Synthesis Step: Preparation of 1,2-diaminocyclohexane-diiodo-platinum(II)

Reaction of potassium tetrachloroplatinate (K$_2$[PtCl$_4$]) with potassium iodide (KI) and 1,2-diaminocyclohexane, whereby first diiodo-compounds are derived in accordance with the formula (2), X=I.

Diagram 1:

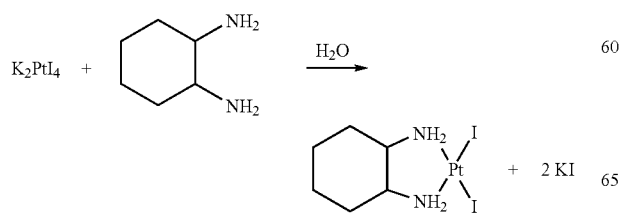

The derived intermediate compound can be introduced after being filtered and washed with water either directly or after being dried in the next reaction step (diagram 2).

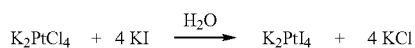

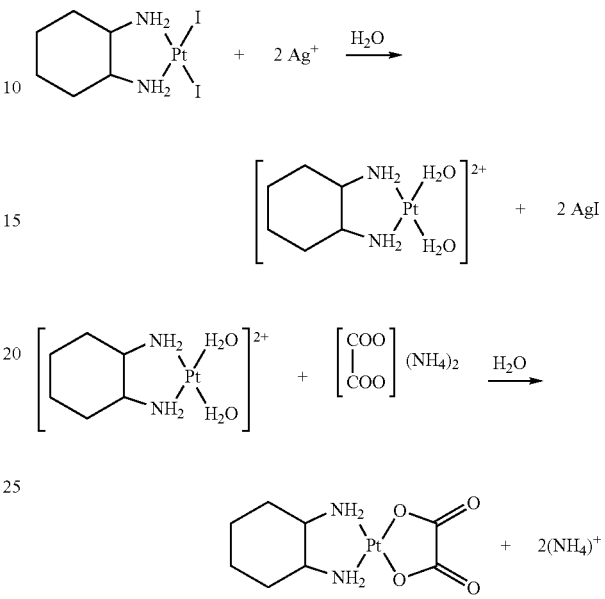

The reaction with soluble silver salt (e.g. silver nitrate, silver sulfate, and such) takes place by resuspending the 1,2-diaminoxycylcohexane-diiodo-platinum(II) (filter cake or dried material) and by adding (based on the platinum quantity used in potassium tetrachloroplatinate) a hypostoichiometric amount, (less than 2 mole equivalents) of soluble silver salt. The hypostoichiometric amount of the soluble silver salt can lie in the range of 1.4 to 1.98 mole equivalents. A preferential amount of soluble silver salt lies in the range of 1.70 to 1.90 mole equivalents. A silver salt quantity in the range of 1.78 to 1.82 mole equivalents is particularly advantageous. The reaction with the silver salt is carried out at temperatures of 20 to 70 degrees C. within 2 to 24 hours. Subsequently the reaction mixture is cooled, preferably for 4 to 30 hours at temperatures of 4 to 10 degrees C. and the resulting silver iodide is removed by filtration.

The thus derived solution of the diaqua compound in accordance with formula (3) [counterion in the illustrated case is nitrate; it can also be sulfate or a similar ion] is mixed with a solution of an excess of ammonium oxalate based on the used silver salt. The amount of ammonium oxalate generally lies in the range of 0.51 to 0.70 molar equivalents. 0.525 to 0.60 molar equivalents are preferred while 0.54 to 0.56 molar equivalents are particularly advantageous. The reaction with ammonium oxalate is carried out preferentially at temperatures of 20 to 70 degrees C. within 2 to 24 hours.

The thus obtained solution is mixed with an amount of 5 to 10 weight percentage of activated carbon, based on the potassium tetrachloroplatinate and agitated for 12 to 72 hours. The activated carbon is removed by filtration. A repetition of the described purification with activated carbon is very advantageous.

The obtained solution is once again filtered via a sterile filter and concentrated to a suitable volume of e.g. less than 10 ml per gram of product.

The obtained solution is filtered, washed and dried. It is beneficial to wash it 1-3 times with water ("purified water" in accordance with EP 4 and/or USP 27 or preferentially "highly purified water" in accordance with EP4, endotoxin-free) and 1-3 times with methanol (or another lightly boiling solvent that is pharmacologically acceptable) and dried at least 24 hours in a sterile air stream (at temperatures between 20 and 50 degrees C. and pressure between 1 bar and $10^{-3}$ bars absolute).

The following example serves for the explanation of the invention without restricting it:

EXAMPLE 1

$K_2[PtCl_4]$ (59.60 g) is dissolved in water (439 ml). Potassium iodide (168.0 g) is dissolved in water (147 ml). Both solutions are purified and stirred for 30 min.

Trans-I-1,2-diaminocyclohexane (18.39 g) is dissolved in water (72 ml.) The solution is added to the platinum-containing solution while stirring and the agitation is continued for 72 hours. The obtained suspension is filtered. The filtered deposit is washed with water six times (200 ml) and subsequently dried. Yield of 1,2-diamonocyclohexane-di-iodoplatinum II: 77.9 g (96%).

The obtained Trans-1-1,2 diaminocyclohexane-diiodo-platinum(II) is suspended in water (1389 ml) and the suspension is heated at 45 degrees C. Silver nitrate (43.91 g) is dissolved in water (139 ml) and this solution is purified with platinum-containing solution. The resulting mixture is agitated for 8 hours at 45 degrees C. The suspension is subsequently cooled within 6 hours at 6 degrees C. and filtered.

Di-ammonium oxalate monohydrate (20.19 g) is dissolved in water (278 mL). Water (3333 mL), ammonium oxalate solution and platinum-containing solution are purified and agitated for 8 hours at 45 degrees C. Subsequently activated carbon is added (3.05 g) and again further agitated for 16 hours. It is filtered and the active carbon treatment is repeated. The obtained solution is then led through a sterile filter into a rotary evaporator and concentrated at 55 to 65 degrees C. in a vacuum to about 110 ml. The obtained suspension is filtered and the deposit is agitated thrice in water (28 ml) for 10 min. Subsequently it is washed thrice with methanol (139 ml). The filtered deposit is dried in sterile air stream for at least 24 hours. Yield of oxalato (trans-1-1,2-diaminocyclohexane) platinum (II): 33.88 g (80%).

What is claimed is:

1. A process for the preparation of diaminocyclohexane-platinum(II)-dicarboxylates comprising the following steps:

B) Converting $K_2PtX_4$ with 1,2-diaminocyclohexane (DACH) to (2):

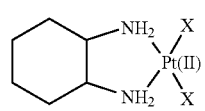

(2)

C) Converting (2) with a silver salt $Ag_nA$ to (3):

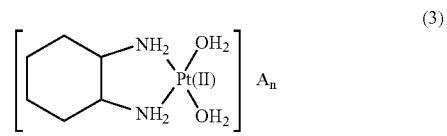

(3)

and removal of the resulting AgX precipitate;

D) Converting (3) with ammonium oxalate to (1):

(1)

F) Isolating the product (1), wherein $R_1$ and $R_2$ together form a dicarboxylato group, X stands for Cl or I, A stands for a 1-2-valent anion of a mineral acid, and n stands for 1 or 2, and wherein in step C an understochiometric amount of silver salt is used.

2. Process in accordance with claim 1, wherein X is I.

3. Process in accordance with claim 2, which is for the preparation of oxalipiatinum, and further comprises the following preceding step:

A) Converting $K_2PtCl_4$ with Kl to $K_2PtI_4$.

4. Process in accordance with claim 1, wherein in step C the mixture is cooled to 1-10 degrees C. before the removal of the precipitate.

5. Process in accordance with claim 1, wherein the solution derived after step D E) is purified twice and filtered with activated carbon.

6. Process in accordance with claim 1, wherein the solution derived after step D or E is concentrated to less than 10 ml/g product.

7. Process in accordance with claim 1, which is conducted in purified endotoxin-free water with limited bacterial content ("purified water" according to European Pharmacopoeia, 4th Edition, and/or U.S. Pharmacopoeia, 27th Edition).

8. Process in accordance with claim 7, whereby the water is "highly purified water" according to EP (European Pharmacopoeia, 4th edition, 2002).

9. Process in accordance with claim 5, wherein the solution derived after step E) is sterilely filtered and then concentrated and F) the solid content is filtered and dried.

10. Process in accordance with claim 1, wherein after step (F)

G) the product is washed with "purified water" according to European Pharmacopoeia, 4th Edition, and/or U.S. Pharmacopoeia, 27th Edition; or "highly purified water" according to European Pharmacopoeia, 4th Edition; and subsequently washed with a light boiling solvent that is pharmacologically acceptable.

11. Process in accordance with claim 10, wherein the solvent is acetone or methanol.

* * * * *